United States Patent [19]
Kilian

[11] 3,962,904
[45] June 15, 1976

[54] PROCESS FOR MEASURING, CONTROLLING AND OPTIMIZING GAS FLOW THROUGH A SINTER MIXTURE ON TRAVELLING GRATES

[75] Inventor: Alois Kilian, Frankfurt am Main, Germany

[73] Assignee: Dravo Corporation, Pittsburgh, Pa.

[22] Filed: June 6, 1975

[21] Appl. No.: 584,582

[52] U.S. Cl. ................................................. 73/38
[51] Int. Cl.² ........................................ G01N 15/08
[58] Field of Search ....... 73/38; 23/230 PC, 253 PC

[56] References Cited
UNITED STATES PATENTS 3,138,014   6/1964   Jorre ....................................... 73/38

FOREIGN PATENTS OR APPLICATIONS 637,967   9/1963   Belgium ................................. 73/38
1,049,205   11/1966   United Kingdom ..................... 73/38

Primary Examiner—Richard C. Queisser
Assistant Examiner—Joseph W. Roskos
Attorney, Agent, or Firm—Parmelee, Miller, Welsh & Kratz

[57] ABSTRACT

A process for measuring, optimizing and controlling the gas permeability of a sinter mixture on a travelling grate by adjusting the flow of air and/or fuel to the furnace to maintain a zero pressure differential between the inside and the outside thereof such that all the gas generated permeates the sinter mixture, and determining the gas permeability as a function of said flows. These steps are repeated for various values of selected process parameters having a significant influence on gas permeability, one at a time, in order to determine the value of each parameter which produces optimum gas flow.

14 Claims, 5 Drawing Figures

PROCESS FOR MEASURING, CONTROLLING AND OPTIMIZING GAS FLOW THROUGH A SINTER MIXTURE ON TRAVELLING GRATES

BACKGROUND OF THE INVENTION

1. Field of the Invention

This invention describes a method for measuring, controlling and optimizing the bed permeability of, i.e., gas flow-through, sinter mixes on a travelling grate.

2. Prior Art

The output of a sinter plant depends largely on the rate that gases will flow through the sinter mix on the travelling grate. As the sintering process takes place, the ability of the gases to flow through a given layer of sinter mix depends on the physical or chemical property of the mix or its components, and also on the pretreatment given the sinter mix. Important factors or parameters are the size consist of the mix, the water content and wetability of the components, the types of additives and the proportion of return fines. The permeability of the mix is also dependent on the porosity of the particles, the method of handling while transporting the mix to the machine and the care with which the mix is metered to the sinter machine.

The bed permeability will also depend on the operation of the ignition furnace, as too high a heat input can fuse the surface and seal the bed against air flow. The ignition furnace is the area over the first windboxes where the sinter mix is ignited by hot combustion products introduced in a hood over the bed and the hot gases are induced to flow through the bed by the suction in the windboxes under the bed.

The ignition furnace will consist of an ignition or combustion zone where hot combustion products are used to sinter the surface of the bed. The furnace can also have an additional annealing zone where preheated air is induced to flow through the sintered bed surface to assist the sintering process if desirable.

To achieve maximum sinter machine utilization, the machine speed should be regulated in relation to all factors or parameters that affect bed permeability. The impact of any of the above-mentioned factors will vary with different ore mixtures, so that factors which bear heavily on one type of ore mixture may be relatively insignificant for others.

It has, therefore, been customary to optimize only those factors which have the most influence of bed permeability in a given case to obtain the highest possible machine speed and plant output.

Sinter machine speeds have been adjusted according to flow measurements taken in the area of the actual burn-through point on the sinter machine. Any change in location of the burnthrough point will also change the location of the measurement setup, unless several measurement setpoints have been arranged in the vicinity of the burn-through point. The latter arrangement will permit recognition of changes in burn through, and by adjusting the machine speed, the location of the burn-through point can be changed with respect to the gas flow-through, or bed permeability of, the sinter mix. This method, however, will have no bearing on the actual combustion process, the heat input, and other factors which might influence the ignition zone proper. The cost for one or more adjustable setups to measure gas flow is considerable because separate systems to measure gas flow will be required. (See German Patent No. 1,961,297.)

The impact of humidity on quality and output of sinter plants has resulted in a process to control such moisture additions (See German Patent No. 1,811,281), in order to adjust the gas flow rate of green pellets or sinter mix by measuring such gas flow rates in a separate bin or on the travelling grate before the mix reaches the ignition furnace.

There is, however, no process available by which gas flow in the actual furnace can be controlled for the purpose of output maximization. Yet, this range is the most important part of the entire process because the mode of combustion in this area will control the quality of the sinter to a considerable extent. The machine speed for the combustion process taking place in this zone will determine the outcome of the entire process. Measurements for gas flow by conventional methods appear to be very difficult in a hot gas zone, therefore, it is customary to determine gas flow in front of, or behind, this area with respective instrumentation.

Values that have been established with prior art methods, will yield only relative results, as either derived from one of the given factors or process parameters such as mix moisture content or location of the burn-through point. These values have no bearing on the heat input within the furnace, nor will they accommodate for a change in the rate of gas flow through the sinter mix in the furnace resulting from compression of the mix by the vacuum incurred through suction. Gas flow in the combustion zone will nevertheless remain the determining factor in the reaction of various ore mixtures, their pretreatment, as well as the quality of the sinter product.

SUMMARY OF THE INVENTION

The purpose of this invention is the avoidance of drawbacks experienced with conventional measuring devices. Instead, the various factors or process parameters which influence gas flow in the ignition furnace will be measured and then used for controlling and maximizing the output of the travelling grate and the volume of the sinter thus produced.

This problem will be solved by inducing controlled quantities of hot gas into the sinter mix on the travelling grate in the ignition furnace. The gas will be drawn through the sinter mix in such volumes so as to measure the rate of gas flow of the sinter mix within the ignition furnace. This measured value will then be used to control and to optimize the composition of the mix, its pretreatment ahead of the travelling grate, as well as for the adjustment of the velocity of the travelling grate.

This invention will also make it possible to maximize the gas flow measured in the ignition furnace by way of a gradual change of given factors or process parameters. This method will also control deviations from the nominal rate of gas flow of the sinter mix on the travelling grate.

Gas flow in the furnace range is highly important for the entire sintering process because such flow is part of the actual combustion process. As far as this invention is concerned, no separate gas flow measurement system is required. Only conventional gauges for fuel volume measurement will be used to measure combustion gas, fuel oil, combustion air or preheated air. Attention must be paid to the balance of hot gas volume which must enter the sinter mix from the belt side and must be exhausted in equal quantities from the furnace area. This means that ±0 pressure must prevail in the transition zone between the surface of the sinter mix and the furnace hood. No air should be sucked in, nor should be allowed to escape from, the enclosure. Such pressure balance can easily enough be accomplished with conventional furnace pressure controls. Such methods would, of course, determine the rate of gas flow or bed permeability in terms of a calculated factor which would be derived from the measured and computed gas volume as well as the specific exhaust gas supply or air supply in m³/m²h of sinter surface which equals the rate of gas flow. Any change in a given factor will directly affect the rate of gas flow and will be indicated by a change in the measured gas volume in the furnace. No special gauging system is required. By gradually changing the factors that will influence the process, such as the sinter mix or the moisture content, or by changing the return fines, the temperature of the return fines, the thermal treatment, by increasing or decreasing the machine's speed, or by changing the heat input up to the point of superficial melting of the sinter mix in the combustion zone, curves for maximum gas flow or bed permeability can be plotted. By this method, one can establish the maximum velocity of the sinter machine with maximum gas flow for individual ore mixtures.

This invention can also be used to measure gas flow of sinter mixes through regulation of the furnace pressure by adjusting the air volume in the ignition furnace directly, or by means of a fuel-air ratio control.

By changing the air ratio, one can increase or decrease the input of exhaust gas to suit the supply of air, which will result in a lowering or increasing of furnace temperature. This means that with a furnace pressure of ±0, the exhaust gas supply and the furnace temperature will be adjusted in the ratio of the air content in the exhaust gas. This will determine the optimal gas flow which depends on this ratio in the ignition furnace.

Another preferred application of this invention is for the control of furnace pressure by adjusting the fuel volume at constant air ratio, and thus measure the gas flow-through, or bed permeability of, the sinter mix.

With a known air-gas ratio and when an optimum bed permeability has been determined, the fuel rate will be increased at constant combustion conditions as the sinter machine speed is increased. Increasing the heat input to the furnace can be done up to the point the furnace pressure is ±0. By maintaining a given air ratio, one can adjust the oxygen input for the fuel and the sinter mix accordingly.

This invention can also be used to optimize gas flow through the sinter mix travelling through the ignition furnace in relation to one or several of the following influential factors or process parameters: the thickness of the sinter layer on the belt, the amount of coke and return fines, as well as the moisture content of the mix.

These factors are the most important ones in the majority of cases. The layer thickness constitutes a high flow-through resistance, and with constant machine-length this layer must burn faster, but without reducing sinter quality in order to avoid a reduction in machine speed. The proportion of fuel, as well as the quantity of the return fines, will influence the quality of the sinter produced, similar to the influence of the moisture content of the mix in front of the ignition furnace on the ability of the gas to flow through the bed.

BRIEF DESCRIPTION OF THE DRAWINGS

The following drawings will explain the invention in detail.

DESCRIPTION OF THE PREFERRED EMBODIMENTS OF THE INVENTION

Figure 1:
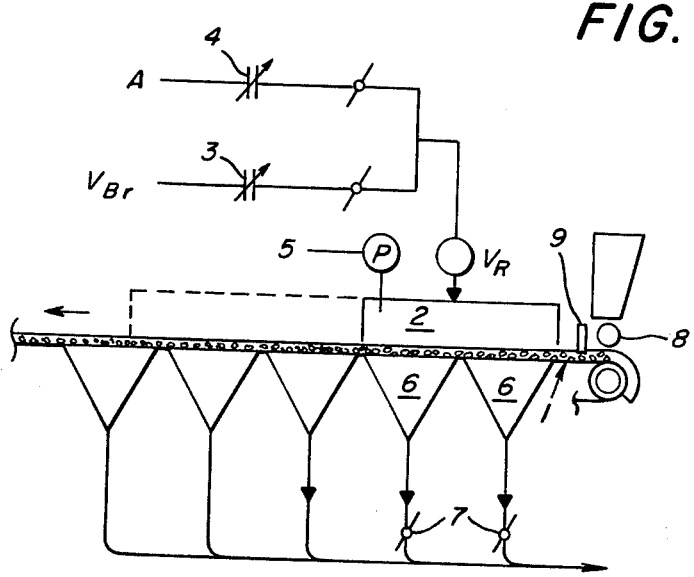
FIG. 1 shows an arrangement of the invention for the measurement of gas flow in the ignition furnace.

In a linear sinter plant according to FIG. 1, with a travelling grate or machine 1 having a length of 100 meters and a width of 4 meters, and an ignition furnace 2 having a length of about 10-11 meters, the gas flow through the sinter mix, or bed permeability, will be determined in terms of the volume of combustion gas generated in the furnace. For this purpose, the gaseous or liquid fuels $V_{Br}$ and the air volume A, which are supplied to the furnace, are measured by gauges 3 and 4 respectively in units of time. These measurements, together with the specific fuel data, are used to determine the combustion gas volume in accordance with the following formula:

$$V_R = V_{Br} [A_o = (\lambda-1) \times 1_o] [Nm^3/h]$$

where $V_R$ = volume of gas flow from the burners after combustion
$V_{Br}$ = fuel flow to the burners
A = air flow to the burners
$A_o$ = specific combustion products from burning fuel stoichiometrically
$1_o$ = specific air requirements for complete combustion of fuel stoichiometrically $$\lambda = \frac{A}{V_{Br} \times 1_o}$$

Gas flow per square meter ($m^2$) of furnace area, or bed permeability, is derived as follows:

$$q_r = \frac{V_R}{B \times L} [\frac{Nm^3}{m^2h}]$$

where
$q_r$ = gas flow per m²
B = width of travelling grate
L = length of furnace While the measurements are being taken, the furnace pressure which is measured by the pressure gauge 5, is adjusted so that no exhaust gas can escape from the furnace, and no atmospheric air can be sucked into the furnace.

Figure 2:
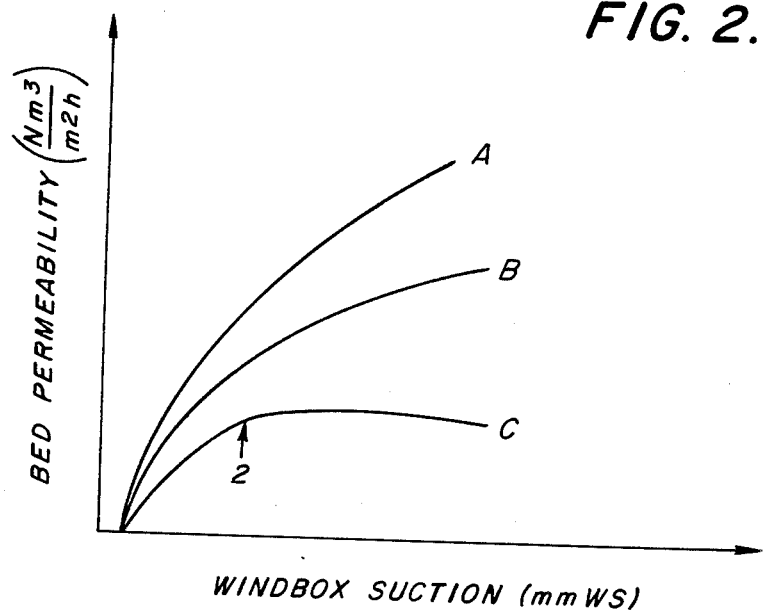
FIG. 2 shows the dependence of gas flow on the vacuum in the windboxes.

According to the above process for the determination of $q_r$, given factors are now gradually changed in order to establish curves defining the relationship between these factors and bed permeability. By gradually changing the vacuum pressure in the windboxes 6 with butterfly valves 7 while maintaining all other conditions constant, the impact of vacuum pressure on gas flow or bed permeability is measured and then plotted as a curve as shown in FIG. 2. FIG. 2 shows the relationship of three different ore mixtures, A, B and C, to the vacuum pressure in the windboxes. The curve will thus show the bed permeability in normal cubic meters per square meter of travelling grate per hour with the windbox vacuum pressure in millimeters water column for a given sinter mix bed thickness.

Figure 3:
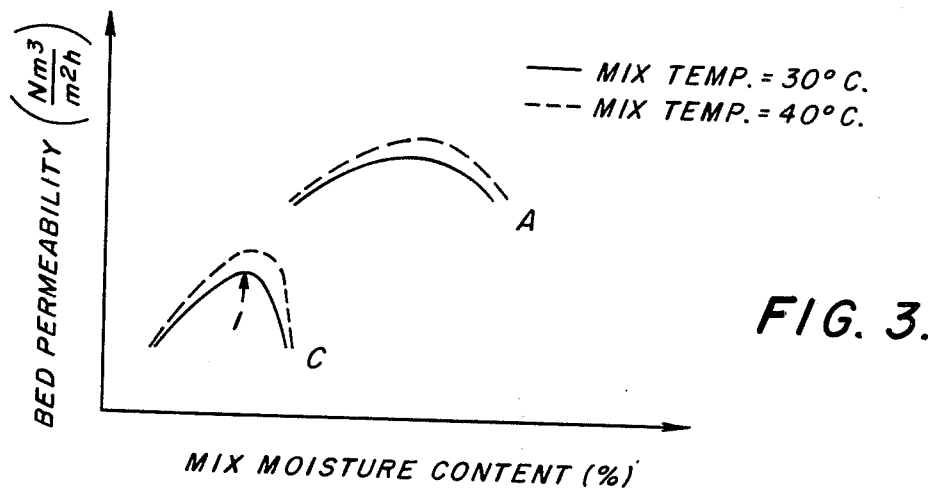
FIG. 3 shows the dependence of gas flow on the sinter mix moisture content and sinter mix temperature.
Figure 4:
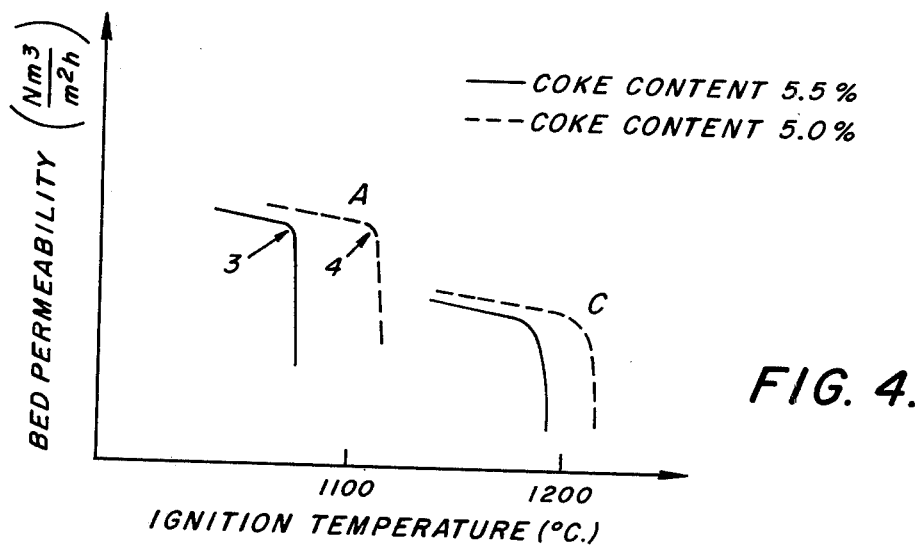
FIG. 4 shows the influence of the ignition intensity on gas flow.

By the same method, one can also determine the actual impact of the mix moisture content and temperature (FIG. 3) as well as the impact of ignition temperature and ignition intensity (FIG. 4).

In the above case for the maximizing of gas flow or bed permeability, the optimal moisture content of ore mixture C was established with a windbox vacuum pressure of 800 mm water column. This mix moisture content was then held constant (see FIG. 3, point 1, on the curve for ore mixture C).

The vacuum pressure in the windboxes was then increased until the maximum rate of gas flow (FIG. 2, point 2, for ore mixture C) was reached.

The exhaust gas temperature in the furnace was then increased until the rate of gas flow began to decrease due to surface fusion of the sinter mix (FIG. 4, point 3). While keeping all other conditions constant, the proportion of coke in the mix was decreased. The exhaust gas temperature in the furnace was then increased until the initial rate of gas flow was regained (FIG. 4, point 4).

Figure 5:
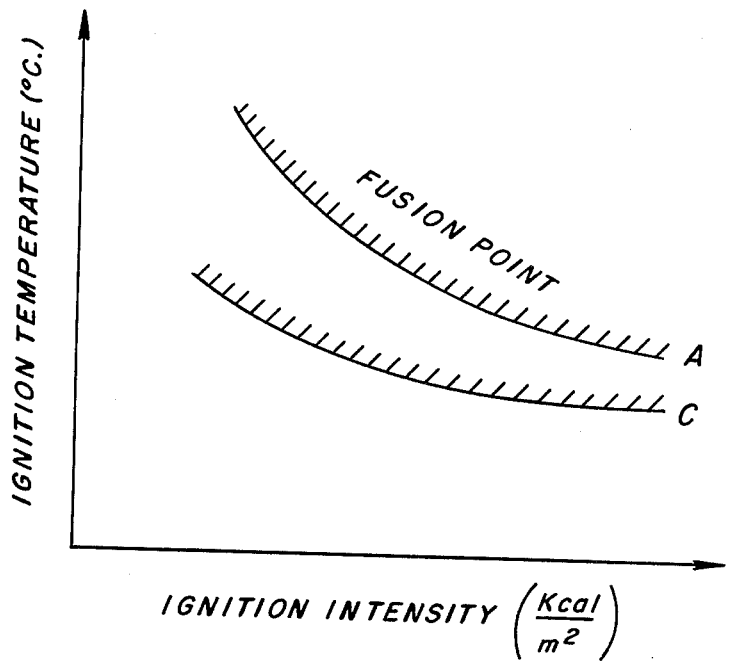
FIG. 5 shows the fusion point curve for ore mixtures A and C, which were derived from the gas flow measurement according to FIG. 4.

The fusion points thus obtained for sinter mixtures A and C with different proportions of coke will thus be dependent upon ignition temperature and ignition intensity as shown in FIG. 5.

This process invention can, therefore, be used to determine optimal gas flow or bed permeability of a given ore mixture in relation to different factors of influence. In the case given above, these factors were windbox vacuum pressure, mix moisture content, ignition intensity, coke rate and furnace temperature. One can equally well consider other factors if they should bear on the process.

I claim as my invention:

1. In a sintering process in which hot gases generated in a furnace by ignition of a fuel-air mixture are drawn by windboxes through the ore-mixture as it passes through the furnace on a travelling grate, the steps of:
   a. determining the gas pressure in the furnace above the grate,
   b. determining the rate of flow of fuel and air to the furnace,
   c. adjusting at least one of said flows to maintain the differential between the gas pressure in the furnace above the grate and the pressure outside the furnace at substantially zero, and
   d. determining the rate of gas flow through the ore-mixture as a function of said flows.

2. The process of claim 1 including the additional steps of
   i. varying any one of a plurality of process parameters
   ii. repeating the steps of claim 1 for the new value of the selected process parameter, and
   iii. sequentially repeating steps i and ii until the selected process parameter has been adjusted to produce optimum gas flow through the ore-mixture 3. The process of claim 2 wherein the process parameter which is varied is the ore-mixture moisture content.

4. The process of claim 2 wherein the process parameter which is varied is the depth of the ore-mixture on the travelling grate.

5. The process of claim 2 wherein the process parameter which is varied is the coke content of the ore-mixture.

6. The process of claim 2 wherein the process parameter which is varied is the vacuum pressure in the windboxes.

7. The process of claim 2 wherein the process parameter which is varied is the temperature of the gases generated by the ignition of the fuel-air mixture.

8. The process of claim 2 wherein the process parameter which is varied is the temperature of the ore-mixture.

9. The process of claim 2 wherein the process parameter which is varied is the return fines content of the ore-mixture.

10. The process of claim 2 including the step of repeating the steps of claim 2 for a second process parameter of said plurality of process parameters.

11. The process of claim 2 including the step of repeating the steps of claim 2 successively for a plurality of said process parameters.

12. The process of claim 1 wherein the flow of fuel is adjusted to maintain the substantially zero differential between the gas pressure in the furnace above the grate and the pressure outside the furnace and wherein the air flow is adjusted to maintain a constant fuel-air ratio.

13. The process of claim 1 wherein the pressure differential between the gas pressure in the furnace above the grate and the pressure outside the furnace is maintained at substantially zero by adjusting the fuel-air ratio.

14. A process for measuring, controlling and optimizing gas flow through a sinter mix on a travelling grate comprising the steps of introducing determinable amounts of hot gas into the furnace of the travelling grate at a rate such that all of the hot gas penetrates and is sucked through the sinter mix by windboxes on the opposite side of the grate,
   adjusting selected parameters affecting gas flow through the sinter mix one at a time to establish for each such parameter the value thereof at which gas flows through the sinter mix at the optimum rate, and
   adjusting the speed of the travelling grate to maintain optimum gas flow.

* * * * *